United States Patent [19]

Dawson

[11] Patent Number: 4,464,389

[45] Date of Patent: Aug. 7, 1984

[54] ESTERS OF RETINOIC ACID AND PENTAERYTHRITOL AND MONOBENZAL ACETALS THEREOF

[75] Inventor: Marcia I. Dawson, Los Altos, Calif.

[73] Assignee: SRI International, Menlo Park, Calif.

[21] Appl. No.: 435,415

[22] Filed: Oct. 20, 1982

[51] Int. Cl.$^3$ .............. A61K 31/335; A61K 31/215; C07C 69/74; C07D 319/06
[52] U.S. Cl. .................................. 424/278; 549/375; 560/128; 424/305
[58] Field of Search ............... 549/375; 424/278, 305; 560/128

[56] References Cited

U.S. PATENT DOCUMENTS

| | | | |
|---|---|---|---|
| 3,781,314 | 12/1973 | Bollag et al. | 560/128 |
| 4,055,659 | 10/1977 | Gander et al. | 424/305 |
| 4,129,662 | 12/1978 | Gander et al. | 424/305 |
| 4,190,594 | 2/1980 | Gander et al. | 424/305 |
| 4,193,931 | 3/1980 | Loeliger | 424/308 |
| 4,200,647 | 4/1980 | Bollag et al. | 424/305 |
| 4,216,224 | 8/1980 | Yu et al. | 424/305 |
| 4,304,787 | 12/1981 | Gander et al. | 424/305 |

FOREIGN PATENT DOCUMENTS 952181  3/1964  United Kingdom ............... 549/375

OTHER PUBLICATIONS

Boutwell et al., Advances in Enzyme Regulation, V. 17, Ed. Weber, G., Pergamon Press, (1979).
Verma, A. K., et al., Cancer Res. 39: 419–427, (1979).
Dawson, M. I. et al., J. Med. Chem. 23: 1013–1022, (1980).
Dawson, M. I. et al., J. Med. Chem. 24: 583–592, (1981).

Primary Examiner—Ethel G. Love
Attorney, Agent, or Firm—Ciotti & Murashige

[57] ABSTRACT

Pentaerythritol retinoates and monobenzal acetals thereof such as (E)-2$_\alpha$-phenyl-5$_\alpha$-hydroxy-methyl-5$_\beta$-retinoyloxymethyl-1,3-dioxane, (E)-2$_\alpha$-phenyl-5$_\beta$-hydroxymethyl-5$_\alpha$-retinoyloxymethyl-1,3-dioxane, and pentaerythritol monoretinoate are disclosed. These retinoids are useful as chemopreventive agents and as therapeutic agents for treating nonmalignant skin disorders.

33 Claims, No Drawings

ESTERS OF RETINOIC ACID AND PENTAERYTHRITOL AND MONOBENZAL ACETALS THEREOF

REFERENCE TO GOVERNMENT GRANT OR CONTRACT

The invention described herein was made in the course of work under grant or contract from the National Institute of Health.

DESCRIPTION

1. Technical Field

The invention is in the fields of retinoid chemistry and chemotherapy. More particularly, the invention relates to esters of retinoic acid and pentaerythritol and certain acetals thereof.

2. Background Art

The progressive loss of the regulation of cellular differentiation by epithelial cells can result in cancer. Retinoic acid and some of its analogues (retinoids) have been investigated as "chemopreventive" agents, that is, agents that interfere with tumor promotion in epithelial cells. Boutwell, R. K.; et al., *Advances in Enzyme Regulation* V. 17, Ed. Weber, G., Pergamon Press (1979); Verma, A. K.; et al., *Cancer Res* (1979) 39:419–427; Dawson, M. I.; et al., *J Med Chem* (1980) 23:1014–1022 and *J Med Chem* (1981) 24:583–592.

Various other retinoids have been reported as having antitumor activity or other biological activity such as activity against skin disorders. U.S. Pat. Nos. 3,781,341, 4,129,662, 4,190,594, 4,193,931, and 4,216,224.

An object of the present invention is to provide novel retinoids that are pharmaceutical agents that are specifically useful as chemopreventive agents and as therapeutic agents for treating nonmalignant skin disorders.

Disclosure of the Invention

The compounds of the invention are retinoic acid esters of the formula:

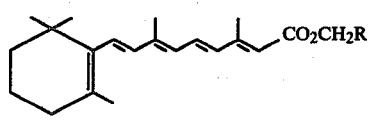

(1)

where R is

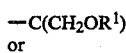

$-C(CH_2OR^1)_3$ or

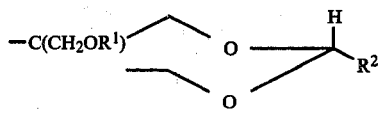

and $R^1$ is individually hydrogen or carbacyl and $R^2$ is phenyl.

When used as pharmaceutical agents one or more of these retinoids is combined with a pharmaceutically acceptable carrier and an effective dose thereof is administered to the patient.

Modes for Carrying Out the Invention

The term "carbacyl" that is used to describe moieties represented by $R^1$ refers to organic radicals derived from carboxylic acid by removal of a hydroxyl group. The carbacyl radicals represented by $R^1$ may be aliphatic, aromatic, cycloaliphatic or heterocyclic. They will typically be monocarboxylic and contain 2 to about 20 carbon atoms, more usually about 2 to about 10 carbon atoms. Preferred acyl groups are alkanoyl of 2 to 10 carbon atoms and retinoyl. Examples of other acyl groups are those derived from straight or branched chain alkanoic or alkenoic acids such as acetoyl, propanoyl, butanoyl, isovaleroyl, hexanoyl, lauroyl, and the like, cyclohexanecarbonyl, cyclohexenecarbonyl, benzoyl, and furoyl.

Examples of retinoids of formula (1) are pentaerythritol monoretinoate, pentaerythritol bisretinoate, pentaerythritol trisretinoate, pentaerythritol tetraretinoate, pentaerythritol acetate monoretinoate, pentaerythritol acetate bisretinoate, pentaerythritol proprionate monoretinoate, pentaerythritol diacetate monoretinoate, pentaerythritol triacetate monoretinoate, pentaerythritol butanoate monoretinoate, pentaerythritol hexanoate monoretinoate, pentaerythritol octanoate monoretinoate, pentaerythritol laurate monoretinoate, pentaerythritol linoleate monoretinoate, pentaerythritol benzoate bisretinoate, pentaerythritol dibenzoate monoretinoate, (E)-2α-phenyl-5α-hydroxymethyl-5β-retinoyloxymethyl-1,3-dioxane, (E)-2α-phenyl-5α-acetyloxymethyl-5β-retinoyloxymethyl-1,3-dioxane, (E)-2α-phenyl-5α-butanoyloxymethyl-5β-retinoyloxymethyl-1,3-dioxane, (E)-2α-phenyl-5α-cyclohexanoyloxymethyl-5β-retinoyloxymethyl-1,3-dioxane, and the like.

The retinoids of formula (1) may be made in the following manner. Retinoic acid is first reacted with an activating agent, such as N,N'-carbonyldiimidazole that forms a retinal imidazole, and a monobenzalpentaerythritol or an acylated monobenzalpentaerythritol. Acylated monobenzalpentaerythritols may be made by reacting monobenzalpentaerythritol with a suitable acyl chloride or activated ester. The reaction between the activated acid and the alcohol is carried out in the presence of a catalytic amount of a strong base such as sodium hydride, in an aprotic solvent at room temperature. The benzal group may be hydrolyzed off to provide the pentaerythritol retinoates. This reaction scheme is depicted below.

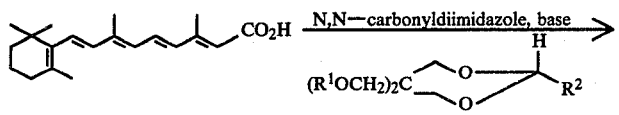

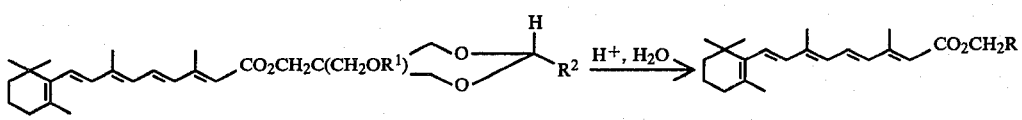

were R, R[1], and R[2] are as defined above.

The following examples illustrate the use of the above described reaction scheme to make representative retinoids of formula (1). These examples are not intended to limit the invention in any manner. The following abbreviations are used in the examples: dimethylformamide=DMF; thin layer chromatography=TLC; high performance liquid chromatography=LC; ethyl=Et;

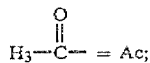

nuclear magnetic resonance=NMR; infrared=IR; ultraviolet=UV; methyl=Me. The subscript R indicates use of the retinoid numbering system.

Example 1. Preparation of
(E)-2α-Phenyl-5α-hydroxymethyl-5β-retinoyloxymethyl-1,3-dioxane (2) and
(E)-2α-Phenyl-5β-hydroxymethyl-5α-retinoyloxymethyl-1,3-dioxane (3)

To a solution of 2.0 g (6.66 mmol) of retinoic acid (4) and 1.3 g (8.02 mmol) of N,N'-carbonyldiimidazole in 15 mL of dry DMF, which had been degassed under argon and stirred at room temperature for 1.5 h, was added a degassed solution prepared from 76 mg (3.2 mmol) of NaH and 3.52 g (15.7 mmol) of monobenzalpentaerythritol (5) in 9 mL of DMF. Stirring was continued for 26 h before the reaction mixture was diluted with 200 mL of $Et_2O$ and washed with two 100-mL portions of water, saturated $NaHCO_3$ and brine, and dried ($MgSO_4$). Concentration at reduced pressure afforded 1.5 g of a yellow foam. The aqueous washes were back-extracted with 200 mL of $Et_2O$, which, in turn, was washed with two 100-mL portions of water and brine, dried ($MgSO_4$), and concentrated at reduced pressure to afford an additional 0.3 g of yellow foam. The crude product [TLC: 20% EtOAc/hexane $R_f$ 0.0, 0.33 [(4) and (5)], 0.48 [(2) and (3)], 0.99; TLC: EtOAc $R_f$ 0.11, 0.14, 0.82 (3), 0.90 (4), 0.97 (retinoic acid would be at 0.32)] was purified by preparative LC (20% EtOAc/hexane) to give 0.65 g (19%) of (2), mp 139°–142° C., and 1.04 g (31%) of (3), mp 135°–137° C., as yellow microcrystalline powders.

Isomer (2): LC (Radialpak B, 20% EtOAc/hexane, 1 mL/min, 326 nm) $t_R$ 9.4 (2%), 11.2 min (98%); LC (Radialpak A, $CH_3CN$, 2 mL/min, 260 nm) $t_R$ 1.8 (0.2%), 3.8 min (99.8%); IR ($CHCl_3$) 3400 (OH), 1700 (C=O), 1610, 1580, 1160, 1100, 1040, 970 cm$^{-1}$; 360 MHz $^1$H NMR ($CDCl_3$) δ 1.03 (s, 6, $16_R$, $17_R$ $CH_3$), 1.47–1.49 and 1.60–1.63 (2 m, 2 and 3, $2_R$, $3_R$ $CH_2$, OH), 1.72 (s, 3, $18_R$ $CH_3$), 1.95–2.05 (m, 2, $4_R$ $CH_2$), 2.01 (s, 3, $19_R$ $CH_3$), 2.37 (s, 3, $20_R$ $CH_3$), 3.82 (d, J=11.6 Hz, 2, axial H), 3.96 (d, J=5.7 Hz, 2, axial $CH_2OH$), 4.02 (s, 2, equatorial $CH_2O_2C$), 4.16 (d, J=11.7 Hz, 2, equatorial H), 5.45 (s, 1, OCHO), 5.79 (s, 1, $14_R$ C=CH), 6.16 (d, J=11 Hz, 1, $10_R$ C=CH), 6.18 (d, J=15 Hz, 1, $8_R$ HC=CH), 6.30 (d, J=15 Hz, 2, $7_R$, $12_R$ HC=CH), 7.05 (dd, $J_{10,11}$=11 Hz, $J_{11,12}$=15 Hz, 1, $11_R$ HC=CH), 7.2–7.48 (m, 2, 3'H, 5'H), 7.36–7.49 and 7.37–7.50 (2 m, 3, 2'H, 4'H, 6'H); $^{13}$C NMR ($CDCl_3$) 12.9 ($19_R$), 14.2 ($20_R$), 19.3 ($3_R$), 21.6 ($18_R$), 29.0 (16R, $17_R$), 33.2 ($4_R$), 34.4 ($1_R$), 38.9 ($CO_2CH_2C$), 39.9 ($2_R$), 61.5 ($CO_2CH_2$), 63.2 ($CH_2OH$), 69.7 ($CH_2OCHOCH_2$), 101.9 (OCHO), 117.2 ($14_R$), 126.1 (2', 6'),* 128.2 (3', 5'),* 128.9 (4'), 129.1 ($7_R$), 129.3 ($10_R$), 130.1 ($5_R$), 131.6 ($11_R$), 134.8 ($12_R$), 137.2 ($8_R$), 137.9 ($6_R$), 138.3 (1'), 140.1 ($9_R$), 154.2 ($13_R$), 167.0 ppm ($15_R$); UV (EtOH) $\lambda_{max}$ 356 nm ($\epsilon 4.88 \times 10^4$); MS calcd for $C_{32}H_{42}O_5$ 506.3032, found 506.3028.

Isomer (3) LC (Radialpak B, 20% EtOAc/hexane, 1 mL/min, 326 nm) $t_R$ 19.6 (shoulder, 2.4%, 17.4 min (97.6%); LC (Radialpak A, $CH_3CN$, 2 mL/min, 260 nm) $t_R$ 1.5 (0.5%), 3.8 min (99.5%); IR ($CHCl_3$) 3400 (OH), 1700 (C=O), 1620, 1580, 1160, 1100, 970 cm$^{-1}$; 360 MHz $^1$H NMR ($CDCl_3$) δ 1.03 (s, 6, $16_R$, $17_R$ $CH_3$), 1.45–1.49 and 1.59–1.69 (2 m, 2 and 2, $2_R$, $3_R$, $CH_2$), 1.72 (s, 3, $18_R$ $CH_3$), 1.97–2.04 (m, 2, $4_R$ $CH_2$), 2.01 (s, 3, $19_R$ $CH_3$), 2.37 (s, 3, $20_R$ $CH_3$), 2.93 (t, J=8 Hz, 1, OH), 3.28 (d, J=8 Hz, 2, equatorial $CH_2OH$), 3.77 (d, J=13 Hz, 2, axial H), 4.17 (d, J=13 Hz, 2, equatorial H), 4.66 (s, 2, axial $CH_2O_2C$), 5.44 (s, 1 OCHO), 5.83 (s, 1, $14_R$ C=CH), 6.15 (d, J=16 Hz, 1, $8_R$ HC=CH), 6.15 (d, J=11 Hz, 1, $10_R$ C=CH), 6.29 (d, J=16 Hz, 2, $7_R$, $12_R$ HC=CH), 7.05 (dd, $J_{10,11}$=11 Hz, $J_{11,12}$=16 Hz, 1, $11_R$ HC=CH), 7.26–7.47 (m, 2, 3'H, 5'H), 7.35–7.49 and 7.35–7.48 (2 m, 3, 2'H, 4'H, 6'H); $^{13}$C NMR ($CDCl_3$) 12.9 ($19_R$), 14.2 ($20_R$), 19.4 ($3_R$), 21.6 ($18_R$), 29.0 ($16_R$, $17_R$), 33.2 ($4_R$), 34.4 ($1_R$), 39.3 ($CO_2CH_2C$), 39.9 ($2_R$), 62.1 ($CO_2CH_2$), 62.7 ($CH_2OH$), 70.3 ($CH_2OCHOCH_2$), 102.2 (OCHO), 117.4 ($14_R$), 126.2 (2', 6'),* 128.2 (3',5'), *128.9 (4'), 129.1 ($7_R$), 129.3 ($10_R$), 130.1 ($5_R$), 131.6 ($11_R$), 134.8 ($12_R$), 137.2 ($8_R$), 137.9 ($6_R$), 138.3 (1'), 140.1 ($9_R$), 154.2 ($13_R$), 167.9 ppm ($15_R$); UV (EtOH) $\lambda_{max}$ 356 nm ($\epsilon 4.56 \times 10^4$); MS calcd for $C_{32}H_{42}O_5$ 506.3032, found 506.3028.
*Assignments can be reversed.

Example 2. Preparation of Pentaerythritol Monoretinoate (6)

To 0.505 g (1.00 mmol) of monobenzalpentaerythritol monoretinoate (3) was added 10 mL of MeOH, 25 mL of 1:4 10% hydrochloric acid/MeOH, and 13 mL of $CHCl_3$. The mixture was degassed and stirred at room temperature. After 15 min a clear solution resulted. After 5 h, TLC [EtOAc $R_f$ 0.52 (6) 0.94 ($C_6H_5CHO$), 0.96 (3)] indicated that the spot corresponding to the product was not increasing in size, therefore the reaction mixture was diluted with 100 mL of $H_2O$ and extracted with 200 mL and then 100 mL of EtOAc. The extracts were washed with $H_2O$ (2×50 mL), $NaHCO_3$ (2×50 mL), (50 mL), and brine (2×50 mL). They were then dried ($Na_2SO_4$) and concentrated at reduced pressure to yield 0.6 g of a yellow gum, which was purified by preparative LC with EtOAc to afford 0.26 g (63%) of (6) as a viscous yellow gum: LC (Radialpak A, MeOH, 2 mL/min, 280 nm) $t_R$ 1.2 (0.7%), 2.2 (shoulder, 1.1%), 3.0 min (98.2%); IR ($CHCl_3$) 3450 (OH), 1650 (C=O), 1605, 1590, 1150, 1015, 960 cm$^{-1}$; $^1$H NMR ($CDCl_3$) δ 1.06 (d, J=0.5 Hz, 6, $16_R$, $17_R$ $CH_3$), 1.40–1.75 (m, 4, $2_R$, $3_R$ $CH_2$), 1.73 (s, 3, $18_R$ $CH_3$), 2.03 (s, 3, $19_R$ $CH_3$), 2.08 (m, 2, $4_R$ $CH_2$), 2.37 (s, 3, $20_R$ $CH_3$), 3.14 (broad s, 3, OH), 3.68 (s, 6, $CH_2OH$), 4.25 (s, 2, $CO_2CH_2$), 5.82 (s, 1, $14_R$ C=CH), 6.17 (d, J=11 Hz, 1, $10_R$ C=CH), 6.19 (d, J=15 Hz, 1, $8_R$ HC=CH), 6.30 (d, J=15 Hz, 2, $7_R$, $12_R$ HC=CH) 7.05 (dd, $J_{10,11}$=11 Hz, $J_{11,12}$=15 Hz, 1, $11_R$ HC=CH); $^{13}$C NMR ($CDCl_3$) 12.9 ($19_R$), 14.1 ($20_R$), 19.2 ($3_R$), 21.7 ($18_R$), 28.9 ($16_R$, $17_R$), 33.1 ($4_R$), 34.3 ($1_R$), 39.6 ($2_R$), 45.5 ($CO_2CH_2C$), 62.1 ($CO_2CH_2$), 63.3 ($CH_2OH$), 117.2 ($14_R$), 129.0 ($7_R$), 129.3 ($10_R$), 130.1 ($5_R$), 131.8 ($11_R$), 134.7 ($12_R$), 137.1 ($8_R$), 137.7 ($6_R$), 140.2 ($9_R$), 154.6 ($13_R$), 168.1 ppm ($15_R$); UV (EtOH) $\lambda_{max}$ 353 nm ($\epsilon 4.86 \times 10^4$); MS calcd for $C_{25}H_{38}O_5$ 418.2719, found 418.2749.

The retinoids of formula (1) may be used topically or systemically as chemopreventive agents and in the treatment, amelioration, or prevention of the skin disorders and rheumatic illnesses for which retinoic acid and other retinoids are useful. In this regard, they may be used for therapy in animals, including humans, of premalignant epithelial cell lesions, as a prophylaxis against tumor promotion in epithelial cells and treatment for dermatoses such as icthyoses, follicular disorders, benign epithelial disorders, and other proliferative skin diseases (nonmalignant conditions of the skin that are characterized by epidermal cell proliferation or incomplete cell differentiation) such as acne, psoriasis, eczema, atopic dermatitis, nonspecific dermatitis and the like. When used for such treatments they will usually be formulated with a pharmaceutically acceptable liquid, semi-solid, or solid carrier. A pharmaceutically acceptable carrier is a material that is nontoxic and generally inert and does not affect the functionality of the active ingredients adversely. Such materials are well known and include those materials sometimes referred to as diluents or vehicles in the pharmaceutical formulation art. The carrier may be organic or inorganic in nature. Examples of pharmaceutically acceptable carriers that may be used to formulate the retinoids are water, gelatin, lactose, starch, mineral oil, cocoa butter, dextrose, sucrose, sorbitol, mannitol, gum acacia, alginates, cellulose, talc, magnesium stearate, polyoxyethylene sorbitan monolaurate, and other commonly used pharmaceutical carriers. In addition to the retinoid and carrier the formulation may contain minor amounts of additives such as flavoring agents, coloring agents, thickening or gelling agents, emulsifiers, wetting agents, buffers, stabilizers, and preservatives such as antioxidants.

For topical administration the retinoids are conveniently provided in the form of ointments, tinctures, creams, solutions, lotions, sprays, suspensions, and the like. The amount of retinoid in such topical formulations will normally be in the range of about 0.01 to about 1% by weight. For enteral (oral or rectal) administration the retinoids will typically be formulated as tablets, capsules, dragees, syrups, solutions, or suppositories. For parenteral administration the retinoids will be formulated as injectable solutions or suspensions.

The dosages and dosage regimen in which the retinoids are administered will vary according to the dosage form, mode of administration, the condition being treated and particulars of the patient being treated. They will, of course, be administered in chemopreventive (tumor promotion inhibiting) amounts or therapeutically effective amounts, as the case may be. For adult humans chemopreventive amounts will usually be about 0.01 mg to 10.0 mg daily given in one or more doses. Oral doses will generally be less than topical doses and doses for treating skin disorders will typically be less than doses administered for chemoprevention. The dose for treating skin disorders will be on the order of the dose of retinoic acid prescribed for the disorder.

The usefulness of the invention compounds was demonstrated by testing the compounds of the Examples in the ornithine decarboxylase (ODC) assay, Verma, A. K. and Boutwell, R. K.; *Cancer Res* (1977) 37:2196–2201, and the tracheal organ culture assay, Newton, D. L.; Henderson, W. R.; and Sporn, M. B.; *Cancer Res* (1980) 40:3413-3425. The ODC assay measures a compound's effect on the prevention of the induction of ODC. The tracheal organ culture assay measures a compound's ability to reverse keratinization.

The ODC assay is carried out as follows. Female Charles River CD-1 mice from Charles River Breeding Laboratories, Wilmington, Mass., are used (age 7 to 9 weeks). The dorsal hair of the mice is shaved 1 to 2 days before testing, and only mice showing no hair regrowth are used. A single dose of 12-O-tetradecanoylphorbol-13-acetate (TPA) (10.5 μg, 17 nmol) in 0.2 mL of acetone is applied topically to the back of each mouse. The test compound, at one of three dose levels (1.7, 17, and 170 nmol), dissolved in 0.2 mL of acetone is applied 1 hour before the TPA treatment to the test groups; the control group is treated with acetone alone. The mice are killed by cervical dislocation five hours after TPA treatment. Determinations are done in triplicate.

The epidermis is obtained from the sacrificed animals. To obtain sufficient material, the dorsal skins from 2 to 3 mice in each treatment group are pooled. The depilatory agent Nudit ® (Helena Rubinstein, New York) is applied to the shaved area of the skin; after 5 minutes, it is washed off thoroughly with cold tap water. Then the skin is excised and plunged immediately into ice-cold water; it is then placed in a 55° C. water bath for 30 seconds and reimmersed in ice-cold water for at least another 30 seconds. The skin is placed epidermis side up on a cold plate, and the epidermis is scraped off with a razor blade. The pooled epidermal sheets are homogenized (Polytron PT-10 homogenizer) at 0° to 4° C. for 15–20 seconds in 50 mM sodium phosphate buffer (pH 7.2) containing 0.1 mM pyridoxal phosphate and 0.1 mM ethylenediaminetetraacetic acid (EDTA), at a volume of 1 mL/skin.

The supernatant fraction remaining after centrifugation of the homogenate at $10,000 \times g$ for 30 seconds at 0° C. is used for the enzyme assay. Enzyme activity is determined using the microassay for ODC as described by Verma and Boutwell to measure the release of $^{14}CO_2$ from DL-[1-$^{14}$C]-ornithine (58 mCi/mmol) after incubation with the $10,000 \times g$ supernatant. The incubations are carried out by decanting, with a Pasteur pipette, 100 μL of the supernatant containing 100 to 120 μg of protein into two or three 15-mL Corex tubes in a shaking water bath at 37° C. The assay mixture in the tubes consists of 50 μL of 100 mM sodium phosphate buffer (pH 7.2), 10 μL of 4 mM pyridoxal phosphate, 40 μL of 25 mM dithiothreitol, and 1 μL of 0.1M EDTA. The center wells in the tubes are filled with 200 μL of a 2:1 solution (v/v) of ethanolamine:2-methoxyethanol. The reaction is started by adding 50 μL of substrate (0.5 μCi of DL-[1-$^{14}$C]-ornithine in 2 mM cold ornithine) at 1-minute intervals by injection to each of the stoppered tubes. Incubations are routinely carried out at 37° C. for 30 to 60 minutes. The reaction is stopped by addition of 0.5 ml of 2M citric acid, and incubation is continued for an additional hour without heating to ensure complete absorption of $^{14}CO_2$.

Radioactivity is measured using a toluene-based scintillant (4 g of PPO and 50 mg of POPOP/L of toluene) in a Beckman LS-250 liquid scintillation counter. Enzyme activity is determined in triplicate and expressed as nanomoles of $CO_2$ released in 30 minutes per milligram of protein. Enzyme activity is linear for the protein concentration used. The protein concentrations of the epidermal extracts are determined by the Lowry procedure, using bovine serum albumin as the standard.

The tracheal organ culture assay is carried out as follows. Tracheas are taken from hamsters that are in very early stages of vitamin A deficiency and placed in organ culture. At the time of culture, the animals are still gaining weight; the tracheal epithelium is generally low columnar or cuboidal, with only occasional patches of squamous metaplasia. Each trachea is opened from the larynx to the carina along the membranous dorsal wall and cultured in a serum-free medium (CMRL-1066; with crystalline bovine insulin, 0.1 μg/ml; hydrocortisone hemisuccinate, 0.1 μg/ml; glutamine, 2 mM; penicillin, 100 units/ml; and streptomycin, 100 μg/ml, added). Cultures are gassed with 50% oxygen, 45% nitrogen, and 5% $CO_2$. The culture dishes are rocked at 35.5–36.0 degrees to allow the tracheas contact with both gas and medium. All tracheas are grown in medium containing no retinoid for the first 3 days. At the end of 3 days, some tracheas are harvested; almost all of these tracheas have significant squamous metaplasia, and approximately 60% have keratinized lesions. The remaining tracheas are then divided into different groups which are treated with either: (1) retinoid dissolved in dimethylsulfoxide (final concentration of DMSO in culture medium is never greater than 0.1%) or (2) an equivalent amount of DMSO alone. Culture medium is changed three times a week, and all of the remaining tracheas are harvested at the end of 10 days in culture. Tracheas are fixed in 10% buffered formalin and embedded in paraffin. Cross sections of five micrometers are made through the mid-portion, stained with hematoxylin and eosin, and then scored with a microscope for the presence of keratin and keratohyaline granules, both of which are found in approximately 90% of control cultures that receive no retinoid for the entire 10 day culture period. Retinoids are scored as "inactive" if both keratin and keratohyaline granules are seen; they are scored as "active" if neither keratin nor keratohyaline granules are seen, or if keratohyaline granules alone are absent.

The table below gives the results of these tests.

|  | Reversal of Keratinization in Hamster Tracheal Organ Culture | | Inhibition of Induction of Ornithine Decarboxylase by 12-O—Tetradecanoylphorbol-13-acetate in Mouse Skin | |
|---|---|---|---|---|
|  | Conc (M) | Active/Total Cultures (%) | Dose (nmol) | % Inhibition of Control |
| Example 1 (Isomer (2)) | $10^{-8}$ | 13/13 (100) | 17 | 49 |
|  | $10^{-9}$ | 17/18 (94) | 1.7 | 40 |
|  | $10^{-10}$ | 9/18 (50) |  |  |
|  | $10^{-11}$ | 2/6 (33) |  |  |
| Example 1 (Isomer (3)) | $10^{-8}$ | 13/13 (100) | 17 | 57 |
|  | $10^{-9}$ | 18/18 (100) | 1.7 | 47 |
|  | $10^{-10}$ | 7/19 (37) |  |  |
|  | $10^{-11}$ | 2/6 (33) |  |  |
| Example 2 | $10^{-8}$ | 13/13 (100) | 17 | 43 |
|  | $10^{-9}$ | 15/15 (100) | 1.7 | 35 |
|  | $10^{-10}$ | 18/25 (72) |  |  |
|  | $10^{-11}$ | 5/11 (45) |  |  |

These results indicate that the retinoids of the invention possess biological activity that makes them useful as chemopreventive agents and therapeutic agents for treating nonmalignant skin disorders.

Modifications of the above described modes for carrying out the invention that are obvious to those of skill in the fields of organic chemistry, pharmaceuticals, and/or medicine are intended to be within the scope of the following claims.

I claim:

1. A retinoic acid ester of the formula:

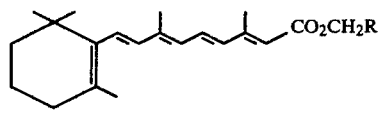

where R is

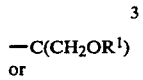

or

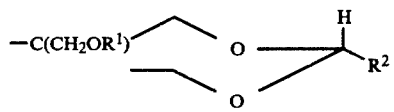

and $R^1$ is individually hydrogen or carbacyl and $R^2$ is phenyl.

2. The retinoic acid ester of claim 1 wherein the carbacyl group is derived from a monocarboxylic acid and contains 2 to about 20 carbon atoms.

3. The retinoic acid ester of claim 1 wherein the carbacyl group is alkanoyl of 2 to 10 carbon atoms or retinoyl.

4. The retinoic acid ester of claim 1 wherein $R^1$ is hydrogen.

5. The retinoic acid ester of claim 4 wherein R is

6. The retinoic acid ester of claim 1 wherein R is

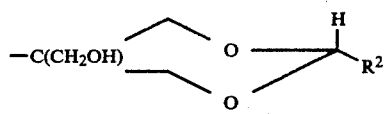

where $R^2$ is phenyl.

7. A chemopreventive composition for inhibiting tumor promotion in epithelial cells in a living animal comprising a tumor promotion inhibiting amount of the compound of claim 1 combined with a pharmaceutically acceptable carrier.

8. A chemopreventive composition for inhibiting tumor promotion in epithelial cells in a living animal comprising a tumor promotion inhibiting amount of the compound of claim 2 combined with a pharmaceutically acceptable carrier.

9. A chemopreventive composition for inhibiting tumor promotion in epithelial cells in a living animal comprising a tumor promotion inhibiting amount of the compound of claim 3 combined with a pharmaceutically acceptable carrier.

10. A chemopreventive composition for inhibiting tumor promotion in epithelial cells in a living animal comprising a tumor promotion inhibiting amount of the compound of claim 4 combined with a pharmaceutically acceptable carrier.

11. A chemopreventive composition for inhibiting tumor promotion in epithelial cells in a living animal comprising a tumor promotion inhibiting amount of the compound of claim 5 combined with a pharmaceutically acceptable carrier.

12. A chemopreventive composition for inhibiting tumor promotion in epithelial cells in a living animal comprising a tumor promotion inhibiting amount of the compound of claim 6 combined with a pharmaceutically acceptable carrier.

13. A therapeutic composition for treating a non-malignant skin disorder comprising a therapeutically effective amount of the compound of claim 1 combined with a pharmaceutically acceptable carrier.

14. A therapeutic composition for treating a non-malignant skin disorder comprising a therapeutically effective amount of the compound of claim 2 combined with a pharmaceutically acceptable carrier.

15. A therapeutic composition for treating a non-malignant skin disorder comprising a therapeutically effective amount of the compound of claim 3 combined with a pharmaceutically acceptable carrier.

16. A therapeutic composition for treating a non-malignant skin disorder comprising a therapeutically effective amount of the compound of claim 4 combined with a pharmaceutically acceptable carrier.

17. A therapeutic composition for treating a non-malignant skin disorder comprising a therapeutically effective amount of the compound of claim 5 combined with a pharmaceutically acceptable carrier.

18. A therapeutic composition for treating a non-malignant skin disorder comprising a therapeutically effective amount of the compound of claim 6 combined with a pharmaceutically acceptable carrier.

19. A method of inhibiting tumor promotion in epithelial cells of a living animal comprising administering a tumor promotion inhibiting amount of the compound of claim 1 to the animal.

20. A method of inhibiting tumor promotion in epithelial cells of a living animal comprising administering a tumor promotion inhibiting amount of the compound of claim 2 to the animal.

21. A method of inhibiting tumor promotion in epithelial cells of a living animal comprising administering a tumor promotion inhibiting amount of the compound of claim 3 to the animal.

22. A method of inhibiting tumor promotion in epithelial cells of a living animal comprising administering a tumor promotion inhibiting amount of the compound of claim 4 to the animal.

23. A method of inhibiting tumor promotion in epithelial cells of a living animal comprising administering a tumor promotion inhibiting amount of the compound of claim 5 to the animal.

24. A method of inhibiting tumor promotion in epithelial cells of a living animal comprising administering a tumor promotion inhibiting amount of the compound of claim 6 to the animal.

25. The method of claim 19 wherein the animal is human.

26. A method of treating a living animal for a non-malignant skin disorder comprising administering a therapeutically effective amount of the compound of claim 1 to the animal.

27. A method of treating a living animal for a non-malignant skin disorder comprising administering a therapeutically effective amount of the compound of claim 2 to the animal.

28. A method of treating a living animal for a non-malignant skin disorder comprising administering a therapeutically effective amount of the compound of claim 3 to the animal.

29. A method of treating a living animal for a non-malignant skin disorder comprising administering a therapeutically effective amount of the compound of claim 4 to the animal.

30. A method of treating a living animal for a non-malignant skin disorder comprising administering a therapeutically effective amount of the compound of claim 5 to the animal.

31. A method of treating a living animal for a non-malignant skin disorder comprising administering a therapeutically effective amount of the compound of claim 6 to the animal.

32. The method of claim 26 wherein the compound is administered topically to the affected area of the skin.

33. The method of claim 26 wherein the animal is human.

* * * * *